United States Patent [19]
Helm et al.

[11] Patent Number: 6,096,021
[45] Date of Patent: Aug. 1, 2000

[54] FLOW ARREST, DOUBLE BALLOON TECHNIQUE FOR OCCLUDING ANEURYSMS OR BLOOD VESSELS

[75] Inventors: Gregory Anthony Helm, Earlysville; David Forest Kallmes; Gerald Robert Hankins, both of Charlottesville, all of Va.

[73] Assignee: The University of Virginia Patent Foundation, Charlottesville, Va.

[21] Appl. No.: 09/281,260

[22] Filed: Mar. 30, 1999

Related U.S. Application Data

[60] Provisional application No. 60/079,975, Mar. 30, 1998.

[51] Int. Cl.$^7$ ..................................................... A61M 31/00
[52] U.S. Cl. .................... 604/509; 604/103.01; 606/194; 606/195; 606/214
[58] Field of Search ............................... 604/509, 96, 101, 604/103.01, 101.01; 606/213–214, 194–195, 108; 623/1

[56] References Cited

U.S. PATENT DOCUMENTS

| | | | |
|---|---|---|---|
| 4,638,803 | 1/1987 | Rand | 128/325 |
| 5,041,090 | 8/1991 | Scheglov et al. | |
| 5,669,924 | 9/1997 | Shaknovich | 606/108 |
| 5,686,115 | 11/1997 | Vournakis et al. | |
| 5,702,361 | 12/1997 | Evans et al. | |
| 5,741,323 | 4/1998 | Pathak et al. | |
| 5,749,894 | 5/1998 | Engelson | |
| 5,752,974 | 5/1998 | Rhee et al. | |
| 5,759,173 | 6/1998 | Preissman et al. | |
| 5,776,099 | 7/1998 | Tremulis | |
| 5,779,673 | 7/1998 | Roth et al. | |
| 5,795,331 | 8/1998 | Cragg et al. | |

OTHER PUBLICATIONS

Szikora et al., "Endovascular Treatment of Experimental Aneurysms with Liquid Polymers: The Protective Potential of Stents," *Neurosurgery* 38(2):339–347 (1996).

Christopher Muther, "Giving surgeons a new tool of the trade," *Boston Globe*, Oct. 11, 1998.

Kinugasa et al., "Cellulose Acetate Polymer Thrombosis for the Emergency Treatment of Aneurysms: Angiographic Findings, Clinical Experience, and Histopathological Study," *Neurosurgery* 34(4):694–701 (1994).

Kinugasa et al., "Early treatment of subarachnoid hemorrhage after preventing rerupture of an aneurysm," *J. Neurosurg.* 83:34–41 (1995).

Ordering Information, Target Therapeutics, Inc., pp. 2–5 (Aug. 23, 1993).

*Primary Examiner*—Mark Bockelman
*Attorney, Agent, or Firm*—Hunton & Williams

[57] ABSTRACT

A method for occluding aneurysms or peripheral blood vessels is provided which allows for isovolumetric, isobaric delivery of occluding agents to aneurysms or peripheral blood vessels, wherein the aneurysms or peripheral blood vessels are isolated from the general circulation until the occluding agent has stabilized or until occlusion is effected. In particular, a double balloon method for occluding aneurysms or peripheral blood vessels is disclosed wherein a first balloon is inserted into the aneurysm or peripheral blood vessel to deliver an occluding agent, and a second balloon is placed such that it substantially covers the neck of the aneurysm or peripheral blood vessel to substantially seal the aneurysm or peripheral blood vessel from the general circulation. Additionally, an aneurysm or peripheral blood vessel comprising a double balloon configuration useful for occluding aneurysms or peripheral blood vessels is disclosed.

26 Claims, 7 Drawing Sheets

FLOW ARREST, DOUBLE BALLOON TECHNIQUE FOR OCCLUDING ANEURYSMS OR BLOOD VESSELS

This application claims benefit to provisional application Ser. No. 60/079,975 filed Mar. 30, 1998.

FIELD OF THE INVENTION

This invention relates to the field of interventional radiology. Specifically, this invention relates to a double balloon method for occluding sites in the vasculature of a patient, such as aneurysms or peripheral vessels. The invention also relates to sites in the vasculature of mammals, particularly humans, which are occluded by a double balloon configuration.

BACKGROUND OF THE INVENTION

Endovascular therapy has long been used in treating a variety of different conditions, including control of internal bleeding, occlusion of blood vessels, and occlusion of aneurysms. A variety of different methods and occluding agents are known for use in such therapy.

Occlusion of blood vessels and aneurysms is preferably accomplished via catheter techniques which permit the selective placement of the catheter at the vascular site to be occluded. In this regard, recent advancements in catheter technology as well as in angiography now permit interventional neuroradiology including the treatment of otherwise inoperable aneurysms. Specifically, development of microcatheters and guide wires capable of providing access to vessels as small as 1 mm in diameter allows for the endovascular treatment of many aneurysms.

Endovascular treatment regimens include the use of occluding devices and occluding agents. One such class of occluding agents includes injectable fluids or suspensions, such as microfibrillar collagen, cellulose acetates, polyvinyl alcohols, and various other polymeric materials. The polymeric agents may be additionally crosslinked, sometimes in vivo, to extend the persistence of the agent at the desired vascular site. These agents are often introduced into the vasculature through the use of a balloon and/or catheter. After such introduction, materials form a substantially solid or semi-solid space-filling mass in the vasculature. There are many problems associated with the current use of the occluding agents, including leakage of the occluding agent into the patient's general circulation, expansion of the aneurysm or vessel volume during introduction of the occluding agent, and possible rupture of the aneurysm or vessel wall.

More common are occluding devices. One such device is a balloon which may be carried to the occluded vessel site at the end of the catheter, inflated with a suitable occluding agent and released from the end of the catheter. The balloon device has the advantage that it effectively fills the cross-section of the occluded vessel. However, when using intravascular balloon occlusion of aneurysms, inflation of a balloon into the aneurysm carries the risk of aneurysm rupture due to possible "overfilling" of portions of the aneurysm cavity. Balloons have also been known to leak the occluding agent into the vasculature during the period before the agent stabilizes.

Various methods for reducing the risks associated with the use of balloons and/or occluding agents have been proposed. One such method, disclosed in U.S. Pat. No. 5,795,331 to Cragg et al., involves inflating a balloon outside of the aneurysm to be occluded, thereby sealing the aneurysm off from the rest of the patient's vasculature. The balloon is positioned such that an injection port is lined up with the neck of the aneurysm to allow for the direct delivery of an occluding agent into the cavity of the aneurysm. In a preferred embodiment, a venting duct is included in the balloon to allow for evacuation of the blood contained in the aneurysm, however, incidents of overfilling and rupture have been reported using this method. For instance, see *Endovascular Treatment of Experimental Aneurysms with Liquid Polymers: The Protective Potential of Stents,* Szikora et al., Neurosurgery, Vol. 38, No. 2, pp. 339–47 (1996).

Despite advances in interventional radiology and endovascular therapy, there remains a need for a method for delivering an occluding agent to an aneurysm or blood vessel, and thereby occluding the aneurysm or blood vessel, which does not significantly increase the volume and/or pressure inside the aneurysm or blood vessel. Further a method is needed which reduces the likelihood of migration of the occluding agent into the vasculature of the patient.

SUMMARY OF THE INVENTION

It is therefore an object of the present invention to provide a method for occluding aneurysms or peripheral blood vessels which eliminates at least some of the problems and deficiencies of prior art.

It is a further object of the present invention to provide an aneurysm or peripheral blood vessel comprising a double balloon configuration useful for occluding aneurysms or peripheral blood vessels.

These and other objects of the present invention will be apparent from the description of the invention which follows.

The present invention addresses the foregoing problems and objects by providing a method for occluding aneurysms or peripheral blood vessels which allows for a substantially isovolumetric, substantially isobaric delivery of an occluding agent to aneurysms or peripheral blood vessels, wherein the aneurysms or peripheral blood vessels are isolated from the general blood circulation until the occluding agent has stabilized or until occlusion is effected.

In particular, the present invention relates to a double balloon method for occluding aneurysms or peripheral blood vessels wherein a first balloon is inserted into the aneurysm or peripheral blood vessel to deliver an occluding agent, and, subsequently, a second balloon is placed such that it substantially covers the neck of the aneurysm or peripheral blood vessel to substantially seal the aneurysm or peripheral blood vessel from the general circulation.

In one embodiment, the present invention relates to a double balloon method for occluding an aneurysm which includes a cavity connected by a neck to a blood vessel (also referred to herein as a "primary blood vessel"), comprising the steps of:

a. introducing a first balloon, via a first catheter, into a cavity of said aneurysm;

b. inflating said first balloon with an occluding agent;

c. introducing a second balloon, via a second catheter, to substantially cover a neck of said aneurysm;

d. inflating said second balloon to substantially seal the cavity of said aneurysm;

e. releasing the occluding agent from the first balloon into the cavity of said aneurysm;

f. maintaining the seal of the cavity of said aneurysm until occlusion is substantially effected, or the occluding agent is substantially stabilized; and g. deflating said second balloon and removing said second balloon and second catheter after occlusion is substantially effected or the occluding agent is substantially stabilized.

In yet another embodiment, the present invention is drawn to a method for occluding a peripheral blood vessel connected by a neck to a primary blood vessel within the vasculature of a patient comprising the steps of:

a. introducing a first balloon, via a first catheter, into said peripheral blood vessel;

b. inflating said first balloon with an occluding agent;

c. introducing a second balloon, via a second catheter, into the primary blood vessel to substantially cover a neck of said peripheral blood vessel;

d. inflating said second balloon to substantially seal the peripheral blood vessel from the primary blood vessel;

e. releasing the occluding agent from the first balloon into the peripheral blood vessel;

f. maintaining the seal of the peripheral blood vessel until occlusion is substantially effected, or the occluding agent is substantially stabilized; and g. deflating said second balloon and removing said second balloon and second catheter after occlusion is substantially effected or the occluding agent is substantially stabilized.

In all embodiments, the occluding agent may be released in any suitable manner, e.g., by rupturing the first balloon. In one embodiment, the sequence of steps of the methods of the invention is that recited above. Nonetheless, the invention includes the step of introducing the second balloon to substantially cover the neck of the aneurysm at any point prior to the release of the occluding agent. For instance, the second balloon can be inserted before the first balloon is inserted and/or guided to the aneurysm cavity; the second balloon can be inserted after the first balloon is in place, but before it is inflated with the occluding agent; or the second balloon can be inserted after the first balloon is in place and inflated with the occluding agent. Regardless of the sequence of steps, it is important that the second balloon be in place and inflated to substantially seal the neck of the aneurysm prior to the release of the occluding agent.

Another aspect of the present invention provides an aneurysm comprising a cavity and a neck leading from a primary blood vessel to said cavity, further comprising a first balloon in said cavity and a second balloon in said primary blood vessel substantially covering said neck, thereby substantially sealing said cavity from said primary blood vessel.

Yet another aspect of the present invention provides a peripheral blood vessel comprising a peripheral vessel body and a neck leading from a primary blood vessel to said peripheral vessel body, further comprising a first balloon in said peripheral vessel body and a second balloon in said primary blood vessel substantially covering said neck, thereby substantially sealing said peripheral vessel body from said primary blood vessel.

DETAILED DESCRIPTION OF THE PREFERRED EMBODIMENTS

Figure 1:
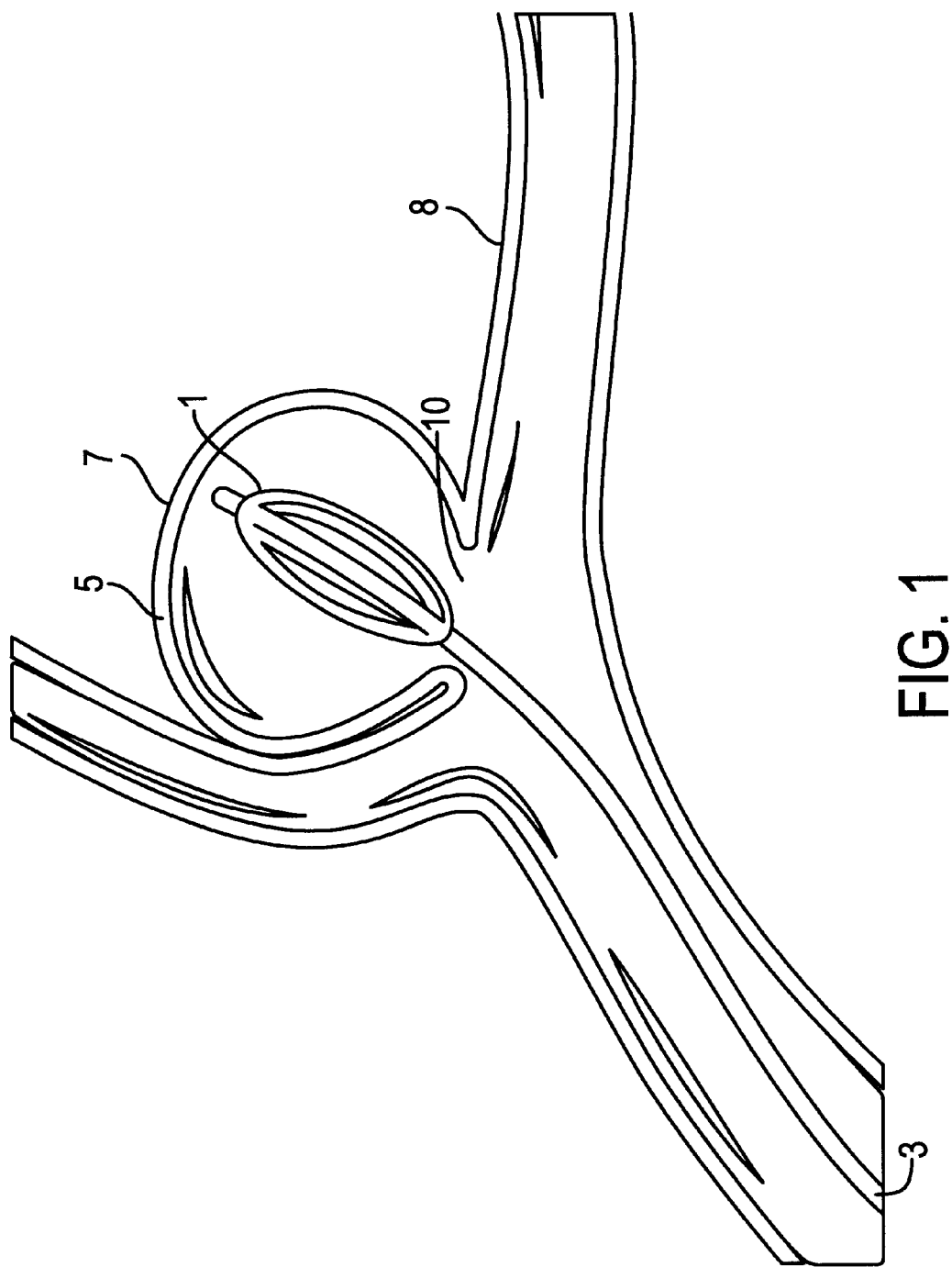
FIG. 1 shows the first balloon inserted in the cavity of an aneurysm.
Figure 2:
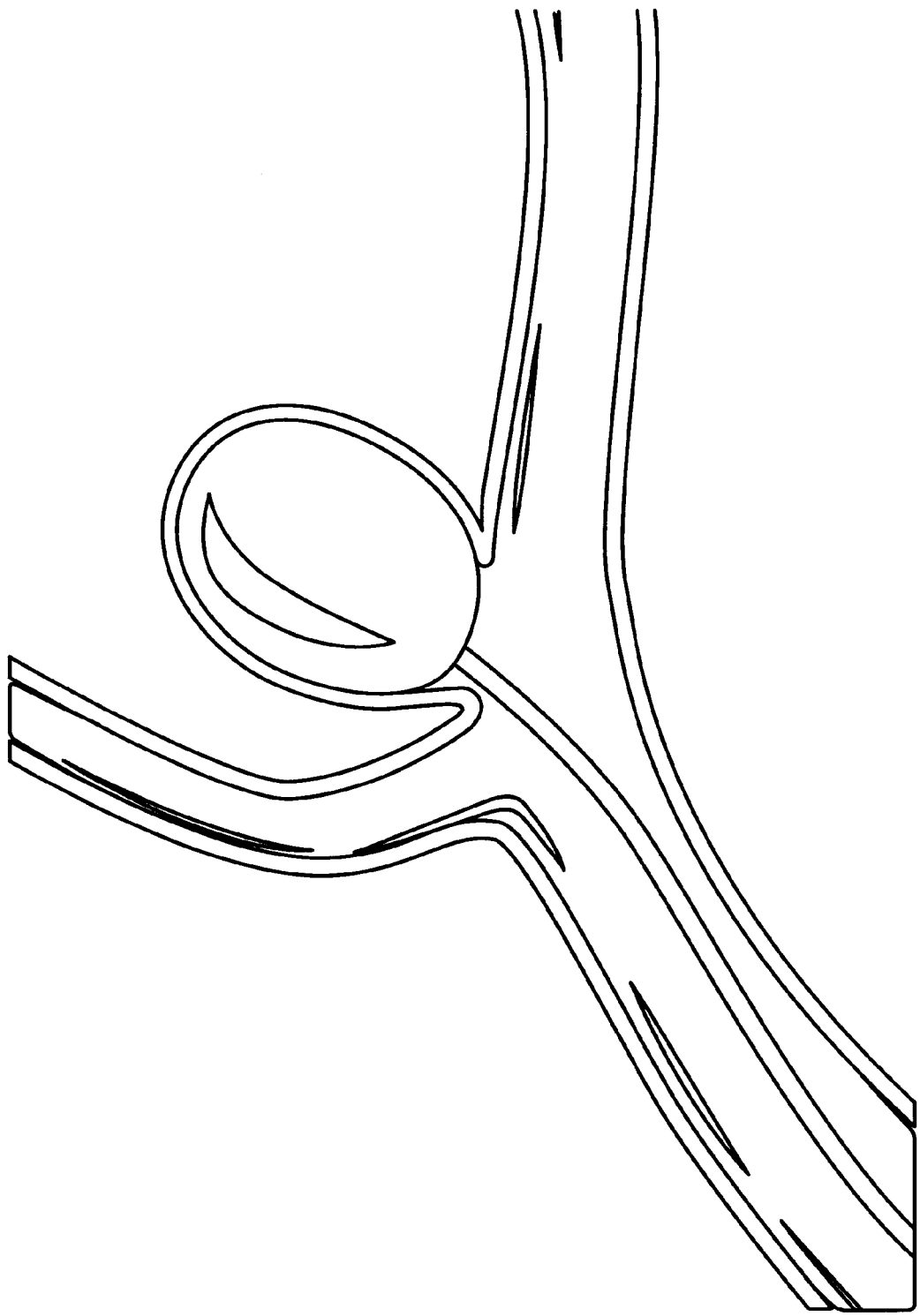
FIG. 2 shows the first balloon in the cavity of the aneurysm after being inflated with an occluding agent.

The term "peripheral blood vessel", includes, without limitation, arterioveneous fistulae ("AVF"), arterioveneous malformations ("AVM") and any blood vessel branching from another vessel, e.g., a primary vessel.

The invention is applicable to the treatment of aneurysms and peripheral blood vessels. While some of the aspects of the invention will be described herein in conjunction with the treatment of an aneurysm, all such aspects can also be utilized in the treatment of a peripheral blood vessel. Some of the aspects of the invention are described herein in conjunction with the drawings of FIGS. 1–7. The drawings represent schematically and generically such aspects of the invention. Nonetheless, the invention is not limited to the aspects of the invention illustrated in the drawings. The scope of the invention is defined by the disclosure, including the claims, considered as a whole.

The invention relates to a double balloon method for occluding an aneurysm or a peripheral blood vessel. The method comprises several steps discussed herein. The first step comprises introducing a first balloon 1, via a first catheter 3, into a cavity 5 of an aneurysm 7 (see FIG. 1) (or a peripheral blood vessel, not illustrated in the drawings), and inflating the first balloon with an occluding agent (see FIG. 2). A main (or primary) blood vessel 8 is connected to the aneurysm through a neck 10. As the first balloon is inflated with the occluding agent, the blood contained within the aneurysm is evacuated and forced out of the cavity of the aneurysm through a neck of the aneurysm without a corresponding substantial increase in aneurysm (or peripheral blood vessel) volume or pressure. The term "without a corresponding substantial increase" means that the volume and pressure within the aneurysm or the peripheral blood vessel are not increased to a degree which may potentially rupture or damage the walls of the aneurysm or the peripheral blood vessel. The first balloon is inflated with the occluding agent by introducing the occluding agent through the first catheter, in a known manner.

Figure 3:
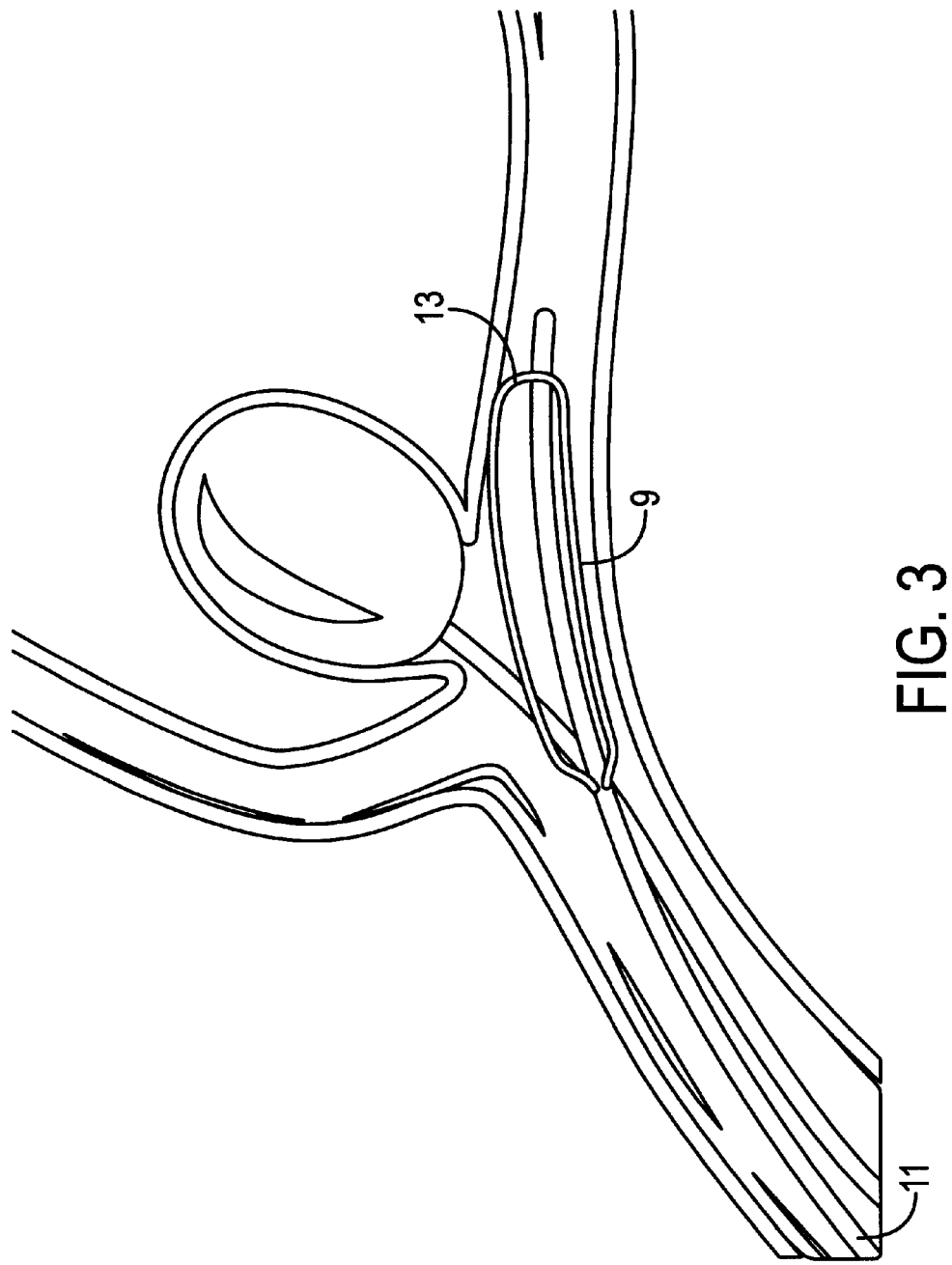
FIG. 3 shows the second balloon, coated with a biocompatible film, inserted to substantially cover the neck of the aneurysm.

Next, a second balloon 9 is introduced, via a second catheter 11, to substantially cover the neck of the aneurysm (see FIG. 3). The second balloon is then inflated to substantially seal the cavity of the aneurysm (see FIG. 4). The second balloon is inflated by any known means, e.g., with a radio-opaque contrast solution introduced through the second catheter. The term "to substantially cover" means that the second balloon is placed such that the neck (or opening) of the aneurysm or peripheral blood vessel to be occluded is covered to such a degree that when the second balloon is inflated, detrimental amounts of the occluding agent are not able to migrate from the aneurysm or peripheral blood vessel into the general blood circulation. Likewise, the term "to substantially seal" means that the second balloon is inflated to such a degree that it prevents detrimental amounts of the occluding agent from migrating from the aneurysm or peripheral blood vessel into a main blood vessel and then into the general blood circulation. The term "detrimental amounts" means amounts sufficient to induce embolisms or occlude other sites within the general circulation and/or vasculature.

Figure 5:
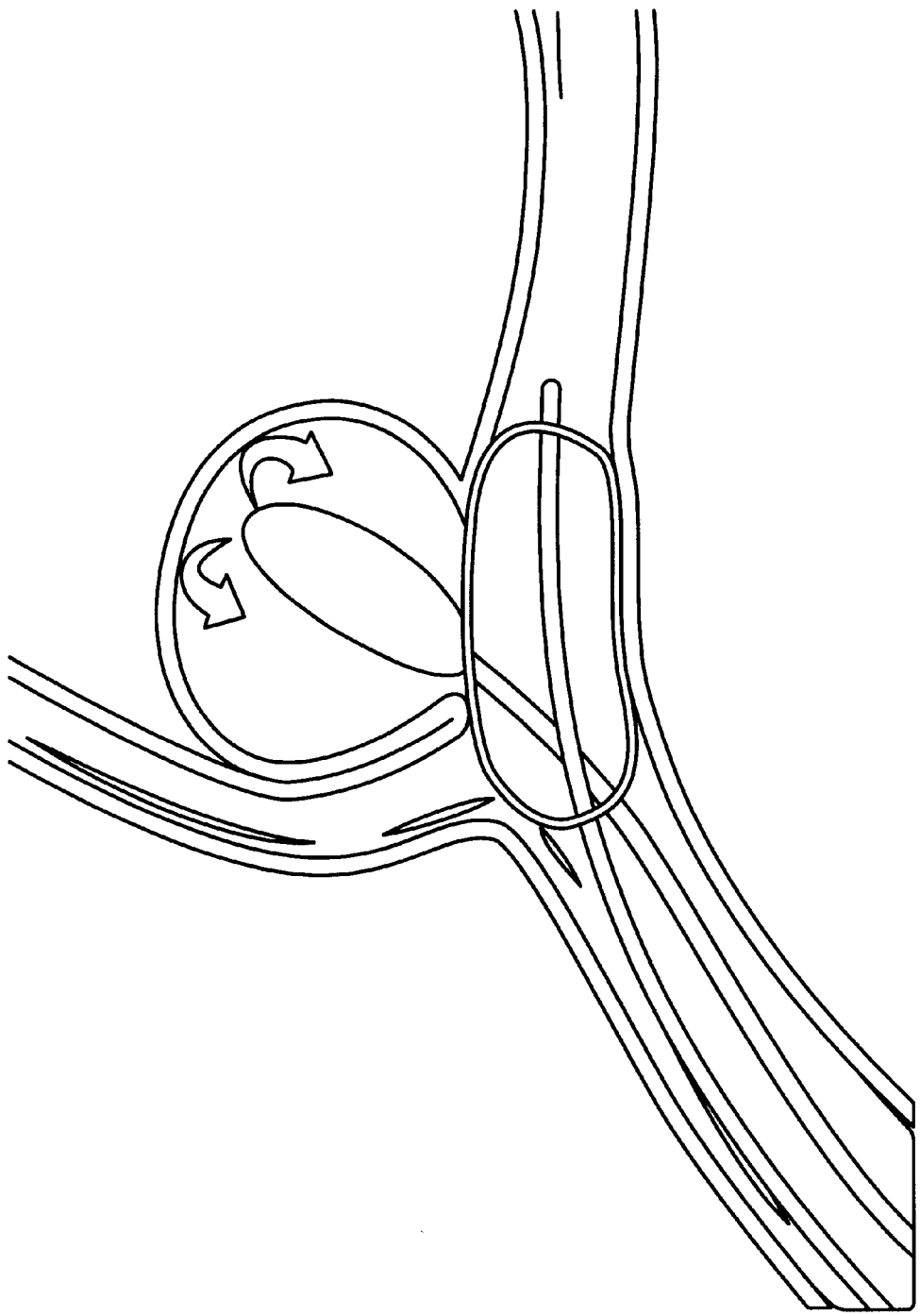
FIG. 5 shows the rupturing of the first balloon in the sealed cavity of the aneurysm, thereby releasing the occluding agent into the cavity of the aneurysm.

Once the second balloon is in place and inflated, the occluding agent is released into the cavity of the aneurysm (see FIG. 5). The occluding agent is released into the cavity of the aneurysm by any method known in the art, preferably by rupturing the first balloon. The term "rupturing" as used herein has the meaning known in the art of treating aneurysms and peripheral blood vessels and usually does not include destruction of the balloon. Thus, the term "rupturing" as used herein means the release of the occluding agent from the first balloon in any technically feasible manner. For instance, the occluding agent can be released from the first balloon by removing the guide wire (e.g., a micro-guide wire) of the first catheter to such a degree that a hole (previously obstructed and sealed by the guide wire) in the first balloon is exposed to enable the occluding agent to escape. This does not, however, destroy the first balloon, which remains intact except for the opening of the hole. Alternatively, the occluding agent may be released into the cavity of the aneurysm in any other known manner, e.g., by the methods disclosed in U.S. Pat. No. 5,741,523 to Patak et al.; U.S. Pat. No. 5,779,673 to Roth et al.; and U.S. Pat. No. 5,041,090 to Scheglov et al.; which are herein incorporated by reference for all purposes and in a manner consistent with this disclosure.

The seal of the neck provided by the second balloon is maintained until occlusion is substantially effected, or the occluding agent is substantially stabilized. In a preferred embodiment, the first balloon and the first catheter can be removed after the occluding agent is released, e.g., by rupturing the first balloon, but before the substantial occlusion or substantial stabilization of the occluding agent has occurred. Alternatively, the first balloon can remain inside the aneurysm. The first balloon can be detached from the first catheter after the occluding agent is released, and then the first catheter can be removed prior to the substantial occlusion or substantial stabilization of the occluding agent.

Various techniques known in the art can be utilized to substantially solidify the occluding agent, and thereby effect substantial occlusion or substantial stabilization of the occluding agent. The terms "occlusion is substantially effected" and "occluding agent is substantially stabilized" and "substantially solidify" (which may also be used interchangeably with the terms "substantial hardening" or "substantial solidification") mean that the occluding agent has been solidified to such an extent that it is sufficiently solid to withstand the shear from the passing blood flow so as to prevent detrimental amounts of the occluding agent from migrating into the general circulation or vasculature.

Suitable techniques for effecting substantial occlusion or substantial stabilization of the occluding agent depend on the type of occluding agent used and can include occlusion or solidification via factors such as heat, radio frequency (R.F.), chemical inducers, ionic interactions (e.g. coagulation in blood); enzymes, visible light, light of other wavelengths, laser, pH or other techniques well known in the art. As stated elsewhere in this application, suitable techniques and the methods of their implementation with balloons and catheters will depend on the particular occluding agent used, as is also known to those skilled in the art. For example, see U.S. Pat. No. 5,749,894 to Engelson; U.S. Pat. No. 5,795,331 to Cragg, et al.; U.S. Pat. No. 5,702,361 to Evans, et al.; U.S. Pat. No. 5,686,115 to Voumakis, et al.; U.S. Pat. No. 5,779,673 to Roth, et al.; and U.S. Pat. No. 5,741,323 to Pathak, et al.; which disclose various such techniques and their implementation and which are all herein incorporated by reference for all purposes and in a manner consistent with this disclosure.

Figure 6:
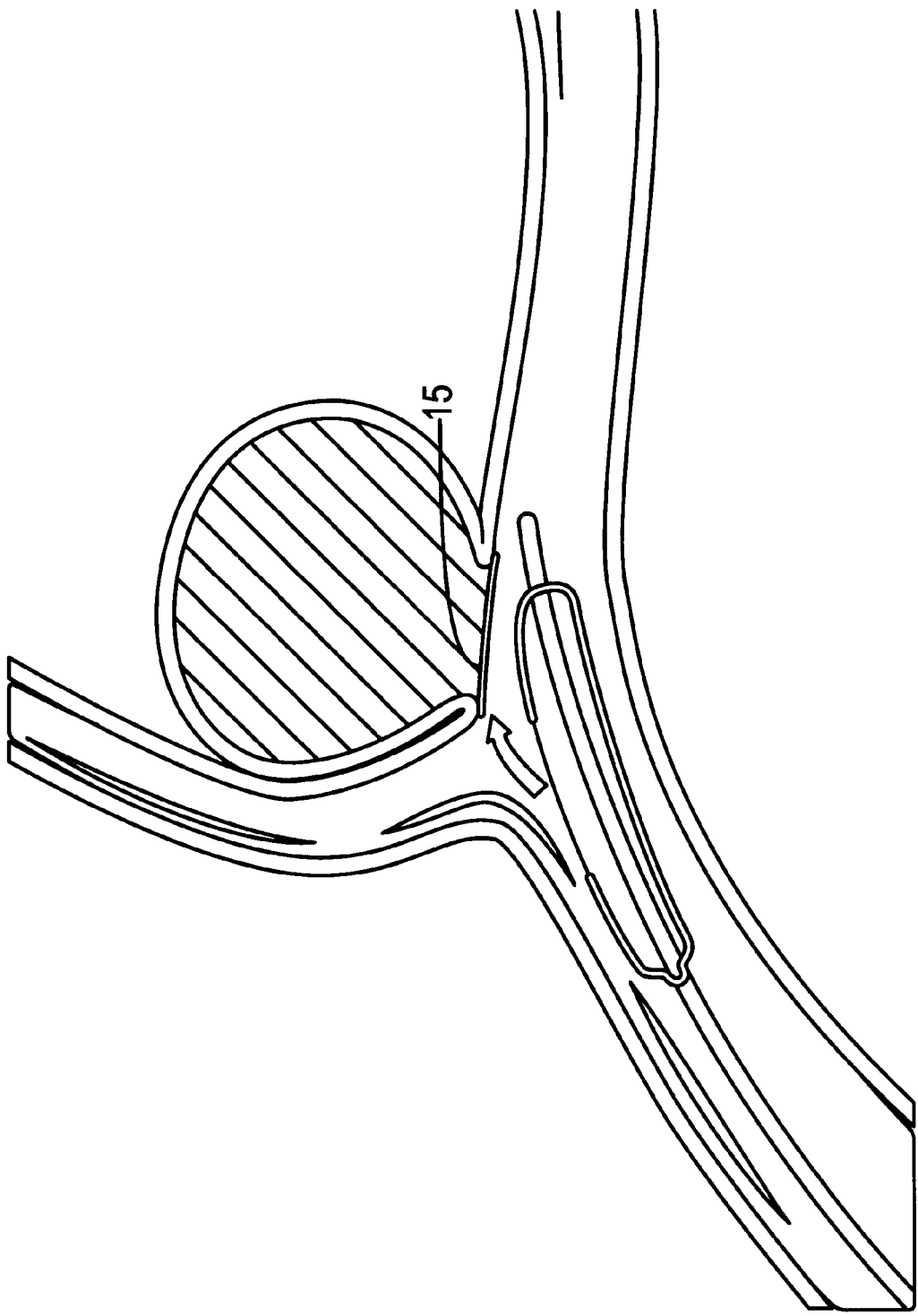
FIG. 6 shows the occluded aneurysm with occluding agent stabilized. Also, the second balloon is deflated and being removed, with a portion of the biocompatible film separated from the second balloon and attached to the outer surface of the occluding agent.
Figure 7:
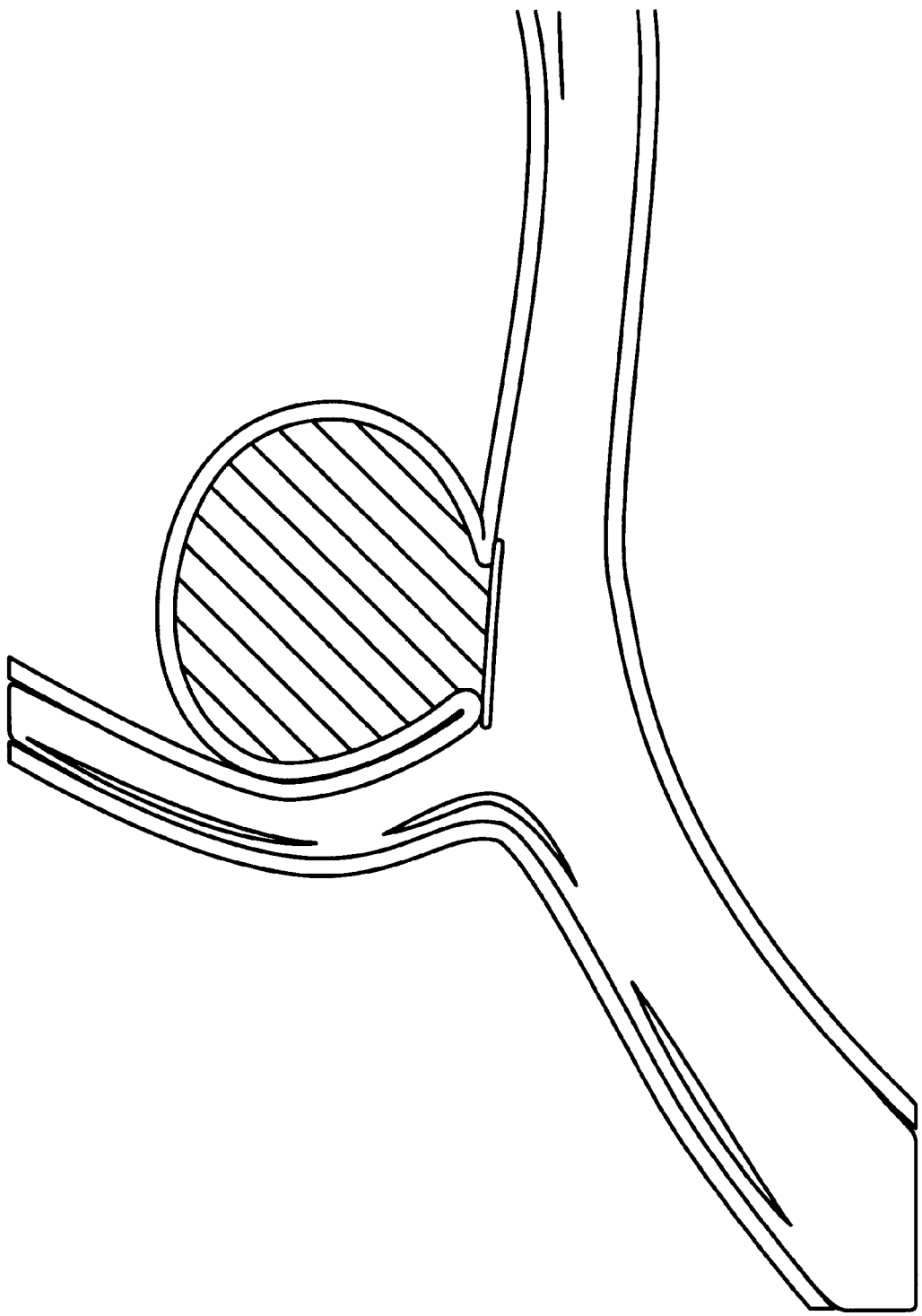
FIG. 7 shows the occluded aneurysm with the occluding agent stabilized and the biocompatible film coating the outer surface of the occluding agent, thereby sealing the occluded aneurysm.

Once occlusion is substantially effected or the occluding agent has substantially stabilized, the second balloon is deflated, and the second balloon and the second catheter are then removed (see FIG. 6). The second balloon is deflated and the second balloon and the second catheter are removed in any manner known in the art.

FIGS. 3 through 7 show a particularly preferred embodiment wherein the second balloon is coated with a biocompatible film 13. This may aid in the removal of the second balloon and to enhance substantial occlusion of the aneurysm. In further embodiments of the invention, the first balloon can also be coated with a biocompatible film if desired. The biocompatible film on the first balloon may also aid in removal of the first balloon from the aneurysm. By way of example, the biocompatible film (of the first and/or second balloon) can comprise at least one biocompatible material selected from cellular adhesion molecules, extracellular matrix proteins, growth factors, hydrogels and silicone. In particular, the biocompatible material can comprise collagen, laminin, fibronectin, elastin, endothelial growth factor ("EGF"), vascular endothelial growth factor ("VEGF"), fibroblast growth factor ("FGF"), or combinations thereof. The biocompatible film on the first balloon may be the same as or different than the biocompatible film on the second balloon. Thus, references to a "biocompatible film" or "biocompatible films" herein include the first and/or the second balloon biocompatible films (unless stated otherwise).

Additionally, the biocompatible films can further comprise a desired cell line. The desired cell line may be obtained from the patient to be treated, or from an established cell line. One possible source of a patient-derived cell line may be autologous dermal fibroblasts. The desired cell line used can include fibroblasts, endothelial cells, muscle cells, stem cells, and mixtures thereof. In preferred embodiments, the desired cell line may be genetically modified by methods generally known in the art, such as disclosed in Sambrook et. al., *Molecular Cloning, A Laboratory Manual*, Second Ed., 1989, pp. 16.30–16.67, which is herein incorporated by reference. The desired cell line can be genetically modified to secrete desired proteins or growth factors such as, but not limited to, transforming growth factors (TGF), fibroblast growth factors (FGF), preferably basic fibroblast growth factors (basic FGF or bFGF), platelet derived growth factors, epidermal growth factors, and mixtures thereof.

In yet other embodiments, the genetically modified cell line can also contain promoters which are inducible in order to control cell proliferation, gene expression, or combinations thereof. For example, it is known that suicide genes, such as those encoding for thymidine kinase, allow selective cell killing under the control of acyclovir. See, for example, Oldfield et al., *Gene therapy of the treatment of brain tumors using intratumolar transduction with the thymidine kinase gene and intravenous gangciclovir*, Hum. Gene Ther. 1993; 4:39–69, which is incorporated herein by reference for all purposes and in a manner consistent with our disclosure. In addition, genes can be regulated under the control of inducible promoters, the activity of which depends on substances such as tetracycline. See Miller et al., *Progress in transcriptionally targeted and regulatable vectors for gene therapy*, Hum. Gene Ther. 1997; 8:803–815, also incorporated herein by reference for all purposes and in a manner consistent with the disclosure.

The desired cell line can be incorporated (or "seeded") into the biocompatible film and coated onto the first or second balloon by any suitable manner. For example, it may involve preliminarily coating the balloon with a biocompatible coating, such as collagen, extracellular matrix proteins, laminin, fibronectin, elastin, or combinations thereof, to enhance cellular adhesion and growth. The coating may have any desirable thickness, so long as it does not impede the growth of the cells and it does not impede the insertion of the balloon into the patient's body. Once the coating is applied to the balloon, the desired cell line can be grown on the coating by incubating the coated balloon with growth media including the desired cell line until the desired level of confluence on the surface of the balloon is obtained. The desired level of confluence means that the cells have grown on the balloon to such an extent as to provide for an adequate degree of cellular proliferation in vivo to enhance the occlusion of the aneurysm or the peripheral blood vessel. The incubation can take place at conditions suitable for the growth of the desired cell line. Incubation conditions can be optimized by methods known in the art and preferably include temperature of 37° C., 95% relative humidity and 5–10% by vol. $CO_2$.

The growth media can be developed by methods well known in the art. For example, one suitable growth medium includes Dulbecco Modified Eagle Medium with 5% fetal bovine serum. The concentration of cells of the desired cell line originally added to the tissue culture dish ("seeding density") can be optimized by methods known in the art. In one embodiment, the seeding density is about $7.5 \times 10^5$ to about $10 \times 10^5$ cells per ml of the growth medium. During incubation, the cells migrate onto the balloon and proceed to grow onto the outer surface of the balloon until the desired level of confluence is obtained.

As used herein, the term "collagen" is intended to encompass collagen of any type, from any source, including, but not limited to, collagen extracted from tissue or produced recombinantly, collagen analogs, collagen derivatives, modified collagens, and denatured collagens.

Without wishing to be bound by any theory of operability, it is believed that the biocompatible film on the second balloon can aid in the removal of the second balloon by forming a barrier between the second balloon and the occluding agent. As occlusion is substantially effected or the occluding agent substantially stabilizes, it is believed that the biocompatible film on the second balloon becomes bonded to that portion of the outer surface of the occluding agent which seals the neck of the aneurysm. Once occlusion is substantially effected or the occluding agent has substantially stabilized, it is preferred that adhesion forces between the biocompatible film on the second balloon and the occluding agent are greater than the cohesive characteristics of the biocompatible film on the second balloon. Then, upon removing the second balloon, at least a portion 15 of the biocompatible film separates from the second balloon and attaches to the aforementioned portion of the occluding agent (see FIG. 6), thereby forming a coating along the outer surface of the occluding agent (see FIG. 7). This coating can improve occlusion and enhance migration, adhesion, and growth of fibroblasts and endothelial cells across the neck of the aneurysm to be occluded. While not wishing to be bound by any theory of operability, it is believed that this cellular migration can improve endothelialization to provide for improved occlusion. The biocompatible film can be applied to the first or the second balloon by methods generally known in the art, and can have any desirable thickness, so long as it does not impede the insertion of the first or the second balloon into the vasculature.

Figure 4:
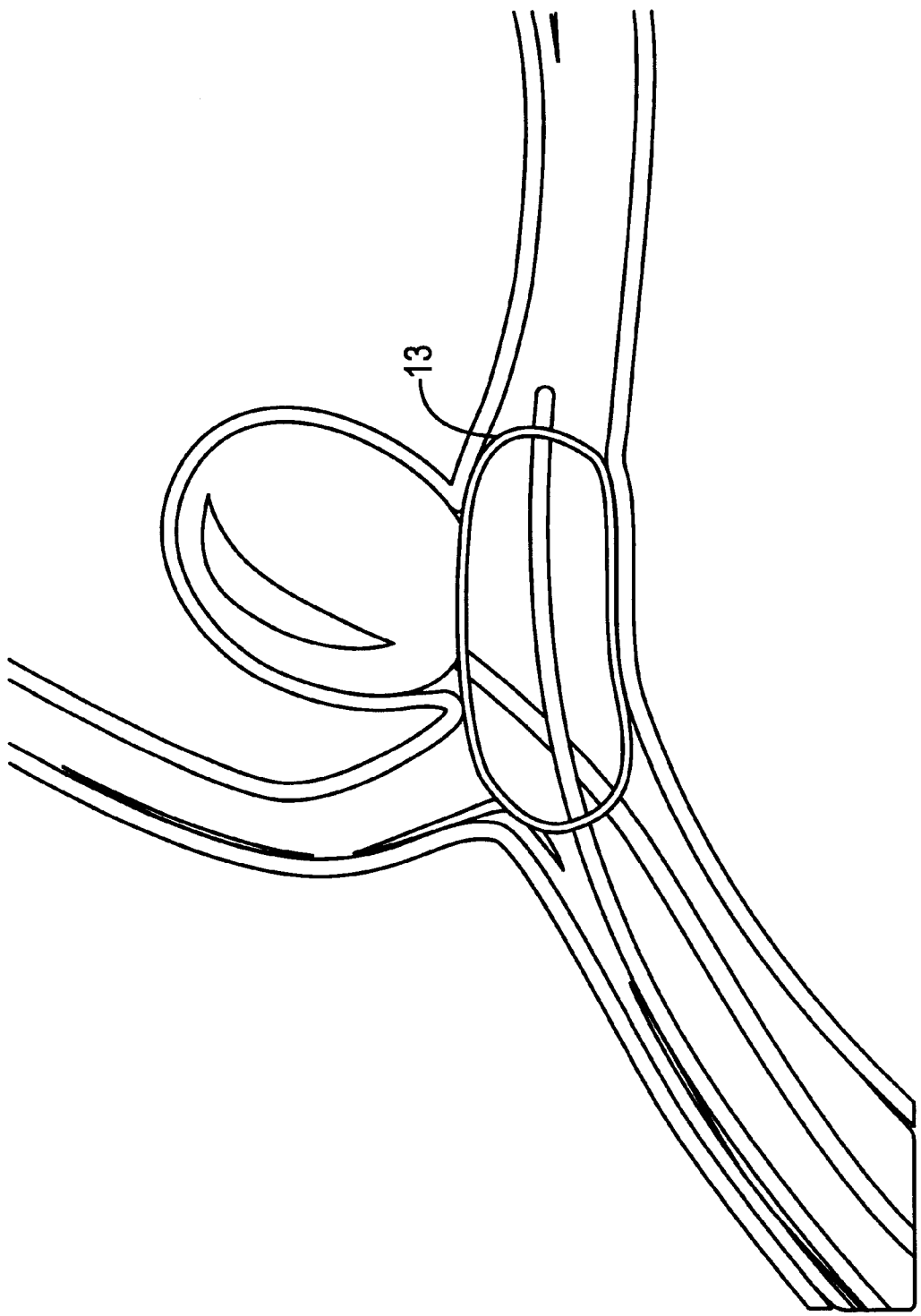
FIG. 4 shows the second balloon inflated to substantially seal the neck of the aneurysm.

Additionally, FIG. 4 demonstrates another aspect of the invention wherein an aneurysm is disclosed which comprises a cavity and a neck leading from a primary blood vessel to the cavity, and further comprises a double balloon configuration with a first balloon inside the cavity of the aneurysm and a second balloon substantially covering the neck, and substantially sealing the cavity. As shown in FIG. 4, the second balloon includes a biocompatible film 13. Nonetheless, the biocompatible film may be omitted.

As discussed above, the present invention can also be used with a peripheral blood vessel. If it is used with a peripheral blood vessel, all of the operative method steps described above for the aneurysm are performed on the respective portions of the peripheral blood vessel. For example, the cavity of the aneurysm which is connected to a primary blood vessel is equivalent to the peripheral vessel body which is connected to a primary blood vessel. The peripheral blood vessel is treated in accordance with this invention to isolate it from the primary blood vessel, thereby cutting off the blood supply to the peripheral blood vessel. Thus, the invention further relates to a corresponding double balloon configuration and method for occluding a peripheral blood vessel connected to a primary blood vessel within the vasculature of a patient comprising the steps of: (a) introducing a first balloon, via a first catheter, into said peripheral blood vessel and inflating said first balloon with an occluding agent; (b) introducing a second balloon, via a second catheter, into the primary blood vessel to substantially cover a neck of said peripheral blood vessel and inflating said second balloon to substantially seal the peripheral blood vessel from the primary blood vessel; (c) releasing the occluding agent into the peripheral blood vessel, e.g., by rupturing said first balloon; (d) maintaining the seal of the peripheral blood vessel with the inflated second balloon until occlusion is substantially effected, or the occluding agent is substantially stabilized; and (e) deflating said second balloon and removing said second balloon and second catheter. All of the modifications, alternatives, parameters and other features of the invention carried out with the aneurysm, discussed herein, are equally applicable to the invention carried out with the peripheral blood vessel.

The first and second balloons and the first and second catheters of the invention may include a wide variety of balloons and catheters known in the art. Further, the balloons and catheters can be inserted into the body, guided to a particular site in the vasculature, and then deflated and removed (if needed) by any suitable method known in the art. Additionally, the first balloon can be detached from the first catheter by methods generally known in the art. For a general discussion of balloons, catheters, and delivery techniques useful in the invention, see U.S. Pat. No. 5,759,173 to Preissman et al., U.S. Pat. No. 5,776,099 to Trmulis, and U.S. Pat. No. 5,041,090 to Scheglov, et al., which are herein incorporated by reference for all purposes and in a manner consistent with this disclosure.

The first balloon is preferably highly compliant to reduce the risk of damaging or rupturing the wall of the aneurysm or peripheral blood vessel to be occluded. For instance, balloons useful in cerebral applications, such as vasospasm angioplasty, are generally acceptable for use as the first balloon of the invention. Such balloons can be constructed from silicon, latex, or analogs thereof. One such balloon was previously marketed by Micro Interventional Systems, Inc., of Sunnyvale, Calif., under the tradename CIROS Particularly, the first balloon is most preferably a monolumen, wire occluding balloon, wherein the balloon comprises a hole that is sealed by placing a guide wire down the lumen of the balloon catheter which abuts the hole to seal it. The monolumen, wire occluding balloon can then be ruptured by removing the guide wire to open the hole and release the occluding agent.

The occluding agent can be any suitable agent known in the art. Preferably, the occluding agent comprises at least one biocompatible polymeric material capable of effecting occlusion through a variety of mechanisms. Preferably, the occluding agent also has adhesive properties to enhance occlusion through bonding with the walls of the aneurysm or peripheral blood vessel. The occluding agent is most preferably introduced as a liquid and is substantially occluded or substantially stabilized within the aneurysm or peripheral blood vessel. In a first variation, the occluding agent may require a reactive catalyst to harden, and the first catheter can comprise a means for separately introducing the catalyst. In a further variation, the occluding agent may react to radiation of a certain wavelength which can be provided from an external source and directed through the lumen of the second catheter to effect substantial occlusion or substantial stabilization of the delivered occluding agent by a light conductor or optical fiber. Alternatively, the occluding agent may be a blood coagulating material which reacts to chemicals, ions, or enzymes contained in blood. For instance, cyanoacrylates substantially stabilize in the presence of ions contained in the blood. If the occluding agent is a blood coagulating material, the first balloon can be inflated to a point where residual blood in the amount necessary to substantially effect occlusion or substantially stabilize the occluding agent remains within the aneurysm or peripheral blood vessel to serve as a solidification agent, once the occluding agent is released into the aneurysm.

The terms "biocompatible polymeric material" and "biocompatible polymer" refer to polymeric materials which, in the amounts employed, are non-toxic, chemically inert, and substantially non-immunogenic when used internally in the patient and which are substantially insoluble in blood. Preferably, the biocompatible polymeric material is also non-inflammatory when employed in situ.

The biocompatible polymeric material (or "biocompatible polymer") can be either a natural biopolymer, or a synthetic biocompatible polymeric material capable of effecting occlusion. For instance, natural biopolymers such as polysaccharides, proteins and peptides can be used as occluding agents. Specifically, laminin, collagen, elastin, fibronectin, fibrin glue, other extra-cellular matrix proteins, or combinations thereof can be used. Additionally, poly-β-1,4-N-acetylglucosamine (p-GlcNAc) polysaccharide species isolated from particular types of algae are useful as occluding agents in the invention. Such polysaccharide species are disclosed, for example in U.S. Pat. No. 5,686,115 to Vournakis, et al., which is herein incorporated by reference for all purposes and in a manner consistent with this disclosure. Further, occluding agents such as those disclosed in U.S. Pat. No. 5,795,331 to Cragg, et al., which is herein incorporated by reference for all purposes and in a manner consistent with this disclosure, are useful in the invention. Additionally, when using natural biopolymers, the occluding agent can further comprise a desired cell line, such as those described above concerning the biocompatible film, to enhance occlusion. The desired cell line can be incorporated into the natural biopolymer by any method generally known in the art. For instance, the natural biopolymer can be co-cultured with the cell line in manner similar to the method disclosed above regarding the biocompatible film, until the desired cell density is obtained.

Suitable synthetic biocompatible polymeric materials include, by way of example, cellulose acetates, polyvinyl alcohols, polyalkenes, polymethacrylates, polyacrylates, cyanoacrylates, polyesters, polyamides, and hydrogels (e.g., acrylics). Preferred synthetic biocompatible polymeric materials include cellulose diacetate and ethylene vinyl alcohol copolymer, cyanoacrylates, hydroxyethyl methacrylate, and silicon. See, for example, U.S. Pat. No. 5,702,361 to Evans, et al.; U.S. Pat. No. 5,749,894 to Engelson; U.S. Pat. No. 5,752,974 to Rhee, et al.; U.S. Pat. No. 5,779,673 to Roth, et al.; and U.S. Pat. No. 5,741,323 to Pathak, et al., which are herein incorporated by reference for all purposes and in a manner consistent with this disclosure, for a general discussion of suitable occluding agents and preparation procedures.

The occluding agent can further comprise a biocompatible solvent and a contrast agent to aid in solubilizing the biocompatible polymeric composition and in delivering the occluding agent to the aneurysm or peripheral blood vessel. Additionally, the occluding agent can further comprise a dye, pigment, or other chromophore to provide the occluding agent with an appropriate color for introduction of energy by laser to effect occlusion or stabilize the occluding agent. For example, see U.S. Pat. No. 5,749,894 to Engelson.

The term "biocompatible solvent" refers to an organic liquid material in which the biocompatible polymer is soluble, at least at the body temperature of the patient to be treated, and, in the amounts used, is substantially non-toxic. Suitable biocompatible solvents include, by way of example, dimethylsulfoxide, analogues homologues of dimethylsulfoxide, ethanol, acetone, and the like. Aqueous mixtures with the biocompatible solvent can also be employed provided that the amount of water employed is sufficiently small such that solidification of the occluding agent is not hindered. Preferably, the biocompatible solvent is dimethylsulfoxide.

The term "contrast agent" refers to a radio-opaque material capable of being monitored during injection into a mammalian subject by, for example, radiography. The contrast agent can be either water soluble or water insoluble. Examples of water soluble contrast agents include metrizamide, iopamidol, iothalamate sodium, iodomide sodium, and meglumine. Examples of water insoluble contrast agents include tantalum, tantalum oxide and barium sulfate, each of which is commercially available in the proper form for in vivo use including a particle size of about 10 $\mu$m or less. Other water insoluble contrast agents include gold, tungsten and platinum. Preferably, the contrast agent is water insoluble (i.e., has a water solubility of less than 0.01 mg/ml at 20. degree. C.).

The occluding agents useful in the invention can be prepared by conventional methods. For example, see U.S. Pat. No. 5,702,361 to Evans, et al.

For instance, an occluding agent can be prepared by adding sufficient amounts of the biocompatible polymeric material to the biocompatible solvent. If necessary, gentle heating and stirring can be used to effect dissolution of the biocompatible polymeric material into the biocompatible solvent (e.g., 12 hours at 50° C.). Sufficient amounts of the contrast agent can then be added. When the contrast agent is not soluble in the biocompatible solvent, stirring can be employed to effect homogeneity of the resulting suspension. The resulting composition can then be heat sterilized and stored, preferably in sealed amber bottles or vials, until needed.

The particular order of addition of components to the biocompatible solvent is not critical and stirring of the resulting suspension is conducted as necessary to achieve homogeneity of the composition. Preferably, mixing/stirring of the composition is conducted under an anhydrous atmosphere at ambient pressure When the biocompatible polymeric material is liquid, the use of a biocompatible solvent is not necessary, but may be preferred to provide for appropriate viscosity and physical properties of the occluding agent.

In a particularly preferred embodiment, the biocompatible polymeric material is cyanoacrylate, which is preferably employed in the absence of a biocompatible solvent. When so employed, the cyanoacrylate is most preferably selected to have a viscosity of from about 5 to about 20 centipoise at 20° C.

The invention will be further described with reference to the following illustrative example.

ILLUSTRATIVE EXAMPLE

A 4 kg New Zealand White Rabbit was prepared. A right femoral cut down was performed, followed by placement of a 6 French guide wire sheath, placed retrograde into the distal aorta. The subject had previously been operated on to create a sidewall aneurysm at the origin of the left renal artery. This is the aneurysm that was used for testing of the double balloon technique concept.

After placement of the guiding catheter, heparin was administered. A standard angioplasty double lumen balloon and catheter were placed through the sheath into the aorta ("parent artery") adjacent to the aneurysm to substantially cover the neck of the aneurysm. Next, a non-detachable silicon balloon ("NDSB") from Interventional Therapeutics Corporation ("ITC") was placed into the aneurysm cavity and inflated with contrast agent.

After the balloon (the first balloon of the invention) within the aneurysm had been inflated, the balloon in the parent artery (the second balloon of the invention) was inflated across the neck of the aneurysm to substantially seal the aneurysm. At this time both balloons were deflated and removed from the subject.

The inflation of the first balloon of the invention demonstrated the ability to replace the blood within an aneurysm with another material in a substantially isovolumetric and isobaric technique, thereby reducing the risk of damaging or rupturing the wall of the aneurysm.

The invention has been described generally, and in connection with the preferred embodiments. These embodiments, however, are merely illustrative and the invention is not restricted thereto. It will be understood by those skilled in the art that other variations and modifications can easily be made which are within the scope of the invention.

What is claimed is:

1. A method for occluding an aneurysm comprising the steps of:
    a. introducing a first balloon, via a first catheter, into a cavity of said aneurysm;
    b. inflating said first balloon with an occluding agent;
    c. introducing a second balloon, via a second catheter, to substantially cover a neck of said aneurysm;
    d. inflating said second balloon to substantially seal the cavity of said aneurysm;
    e. releasing the occluding agent from the first balloon into the cavity of said aneurysm;
    f. maintaining the seal of the cavity of said aneurysm until occlusion is substantially effected, or the occluding agent is substantially stabilized; and
    g. deflating said second balloon and removing said second balloon and second catheter after occlusion is substantially effected or the occluding agent is substantially stabilized.

2. The method of claim 1 wherein said step a, and said step b take place prior to said step c and said step b takes place after said step a, and the remaining steps take place in the order set forth in claim 1.

3. The method of claim 1 wherein said step c takes place after said step a and prior to said step b and the remaining steps take place in the order set forth in claim 1.

4. The method of claim 1 wherein said step c takes place prior to said step a and said step b takes place after said step a, and the remaining steps take place in the order set forth in claim 1.

5. The method of claim 1 wherein the occluding agent comprises at least one biocompatible polymeric material.

6. The method of claim 5 wherein said biocompatible polymeric material is selected from the group consisting of cellulose acetates, polyvinyl alcohols, polyalkenes, polymethacrylates, polyacrylates, cyanoacrylates, polyesters, polyamides, polysaccharides, proteins, and peptides.

7. The method of claim 5 wherein said occluding agent further comprises a radio-opaque contrast agent.

8. The method of claim 1 wherein the occlusion is effected, or the occluding agent is stabilized under conditions which substantially solidify the occluding agent.

9. The method of claim 1 wherein said second balloon is coated with a biocompatible film.

10. The method of claim 9 wherein said biocompatible film separates from the second balloon and attaches to the occluding agent upon removing said second balloon in said step g.

11. The method of claim 9 wherein said biocompatible film comprises at least one biocompatible material selected from the group consisting of cellular adhesion molecules, growth factors, and silicon.

12. The method of claim 1 further comprising the step of:
    e1. removing said first balloon and said first catheter after said releasing in said step e and prior to said occlusion or stabilization of the occluding agent in said step f.

13. The method of claim 1 further comprising the step of:
    e1. detaching said first balloon from said first catheter after said releasing in said step e and removing said first catheter prior to said step f.

14. A method for occluding a peripheral blood vessel connected to a primary blood vessel within the vasculature of a patient comprising the steps of:
    a. introducing a first balloon, via a first catheter, into said peripheral blood vessel;
    b. inflating said first balloon with an occluding agent;
    c. introducing a second balloon, via a second catheter, into the primary blood vessel to substantially cover a neck of said peripheral blood vessel;
    d. inflating said second balloon to substantially seal the peripheral blood vessel from the primary blood vessel;
    e. releasing the occluding agent from the first balloon into the peripheral blood vessel
    f. maintaining the seal of the peripheral blood vessel until occlusion is substantially effected, or the occluding agent is substantially stabilized; and g. deflating said second balloon and removing said second balloon and second catheter after occlusion is substantially effected or the occluding agent is substantially stabilized.

15. The method of claim 14 wherein said step a, and said step b take place prior to said step c, and said step b takes place after said step a, and the remaining steps take place in the order set forth in claim 14.

16. The method of claim 14 wherein said step c takes place after said step a and prior to said step b, and the remaining steps take place in the order set forth in claim 14.

17. The method of claim 14 wherein said step c takes place prior to said step a, said step b takes place after said step a, and the remaining steps take place in the order set forth in claim 14.

18. The method of claim 14 wherein the occluding agent comprises at least one biocompatible polymeric material.

19. The method of claim 18 wherein said biocompatible polymeric material is selected from the group consisting of cellulose acetates, polyvinyl alcohols, polyalkenes, polymethacrylates, polyacrylates, cyanoacrylates, polyesters, polyamides, polysaccharides, proteins, and peptides.

20. The method of claim 18 wherein said occluding agent further comprises a radio-opaque contrast agent.

21. The method of claim 14 wherein the occlusion is effected, or the occluding agent is stabilized under conditions which substantially solidify the occluding agent.

22. The method of claim 14 wherein said second balloon is coated with a biocompatible film.

23. The method of claim 22 wherein said biocompatible film separates from the second balloon and attaches to the occluding agent upon removing said second balloon in said step g.

24. The method of claim 22 wherein said biocompatible film comprises at least one biocompatible material selected from the group consisting of cellular adhesion molecules, growth factors, and silicon.

25. The method of claim 14 further comprising the step of:

e1. removing said first balloon and said first catheter after said releasing in said step e and prior to said occlusion or stabilization of the occluding agent in said step f.

26. The method of claim 14 further comprising the step of:

e1. detaching said first balloon from said first catheter after said releasing in said step e and removing said first catheter prior to said step f.

* * * * *